United States Patent [19]

Flower et al.

[11] Patent Number: 4,863,265

[45] Date of Patent: Sep. 5, 1989

[54] APPARATUS AND METHOD FOR MEASURING BLOOD CONSTITUENTS

[75] Inventors: Ronald J. Flower, Hampstead; Robert W. Olsen, Owings Mills; Michael A. Van Ells, Sykesville, all of Md.; Ralph Flatau, Syracuse, N.Y.

[73] Assignee: Mine Safety Appliances Company, Pittsburgh, Pa.

[21] Appl. No.: 109,760

[22] Filed: Oct. 16, 1987

[51] Int. Cl.[4] ................... A61B 5/00; G01N 33/16
[52] U.S. Cl. .......................... 356/41; 128/633
[58] Field of Search .................. 356/41, 42; 128/633

[56] References Cited

U.S. PATENT DOCUMENTS

| 3,704,706 | 12/1972 | Herczfeld et al. | 356/41 |
| 4,109,643 | 8/1978 | Bond et al. | 356/41 |
| 4,167,331 | 9/1979 | Nielsen | 356/41 |
| 4,266,554 | 5/1981 | Hamaguri | 356/41 |
| 4,407,290 | 10/1983 | Wilber | 356/41 |
| 4,523,279 | 6/1985 | Sperinde et al. | 356/41 |
| 4,621,643 | 11/1986 | New, Jr. et al. | 356/41 |
| 4,651,741 | 3/1987 | Passafaro | 356/41 |

Primary Examiner—Richard A. Rosenberger
Attorney, Agent, or Firm—Walter G. Marple, Jr.; John E. Kidd; Nicholas L. Coch

[57] ABSTRACT

An apparatus for noninvasive determination of constituent concentrations utilizing light wave absorption measurements and methods for processing signals generated by such measurements.

8 Claims, 16 Drawing Sheets

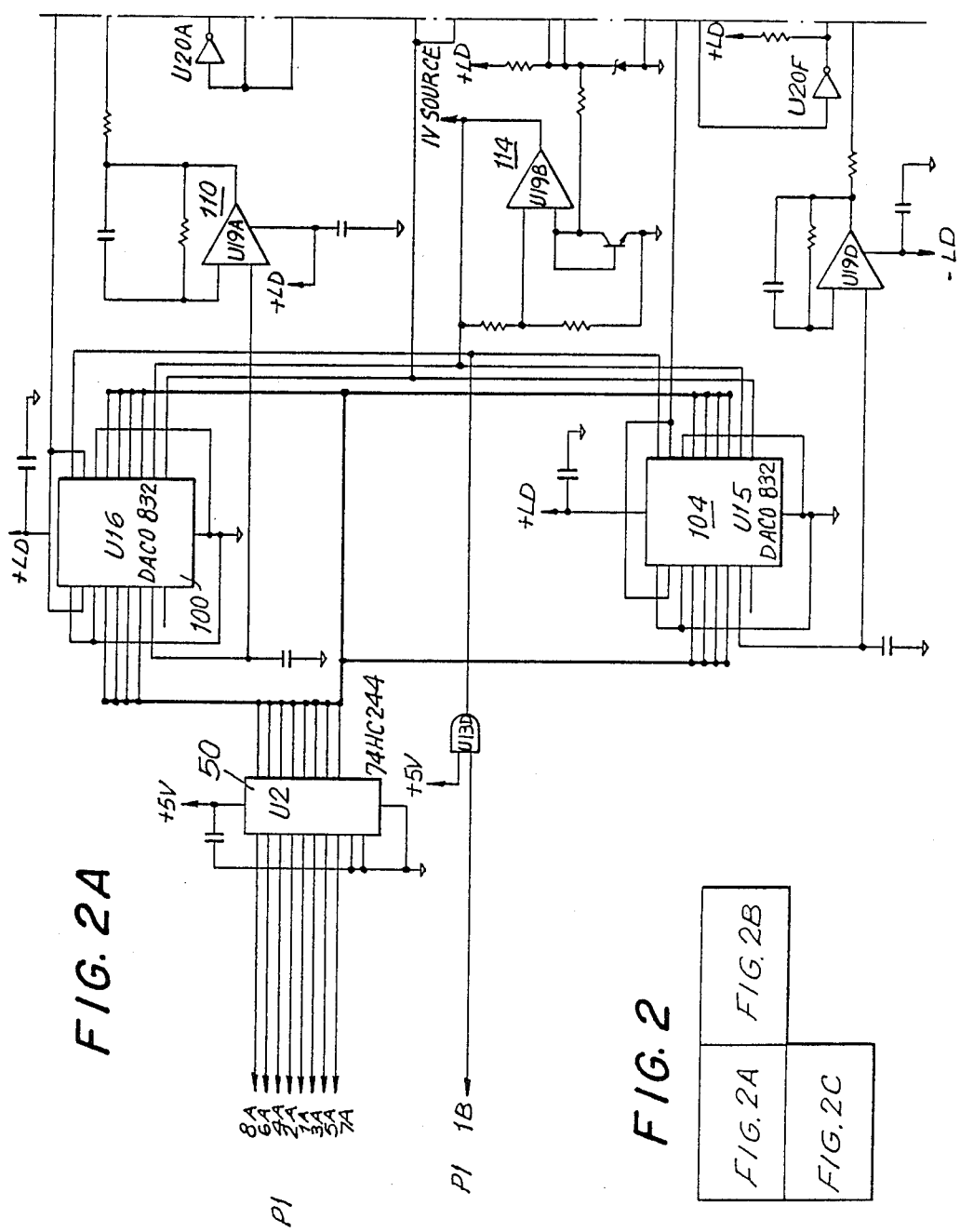

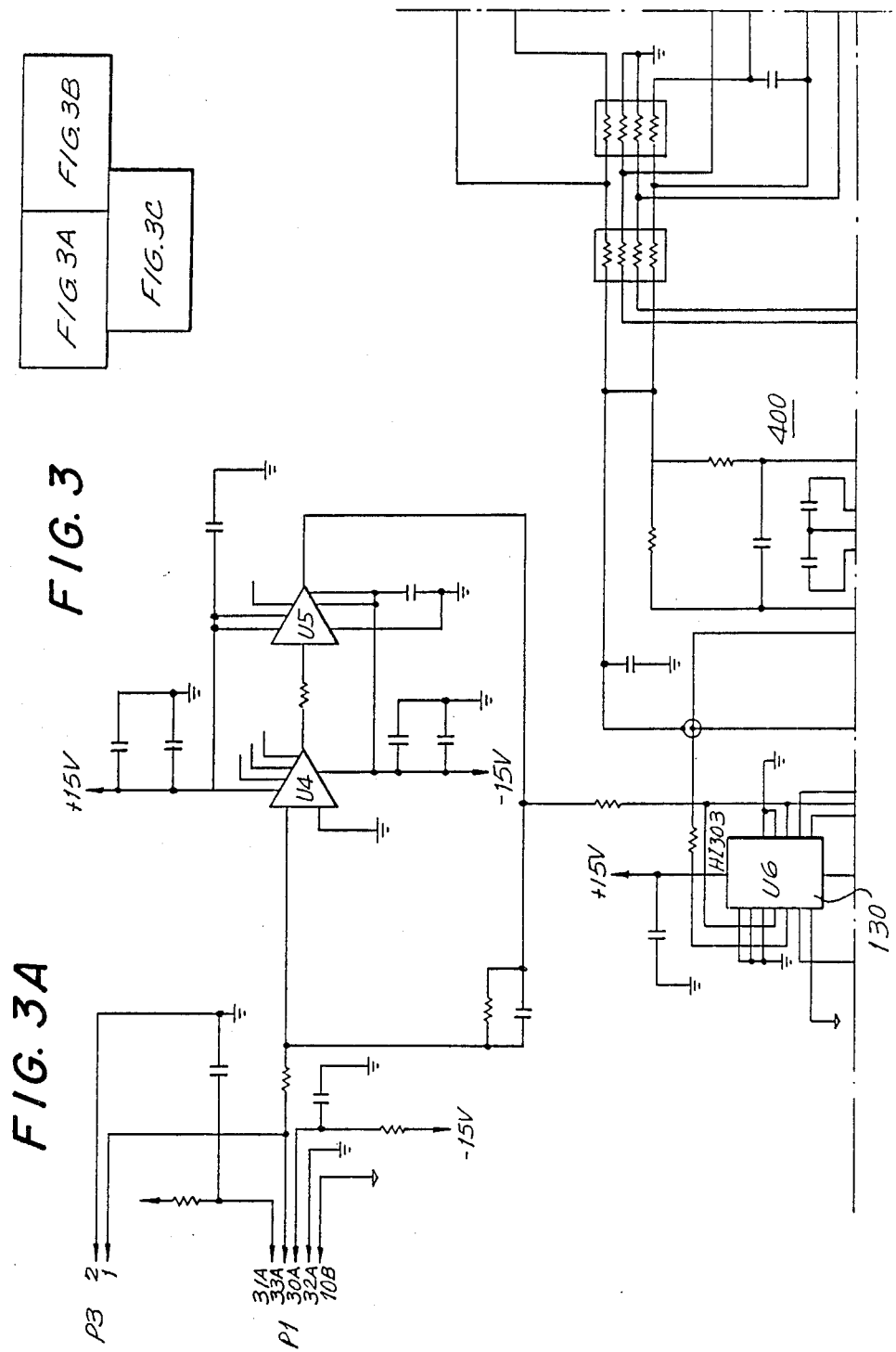

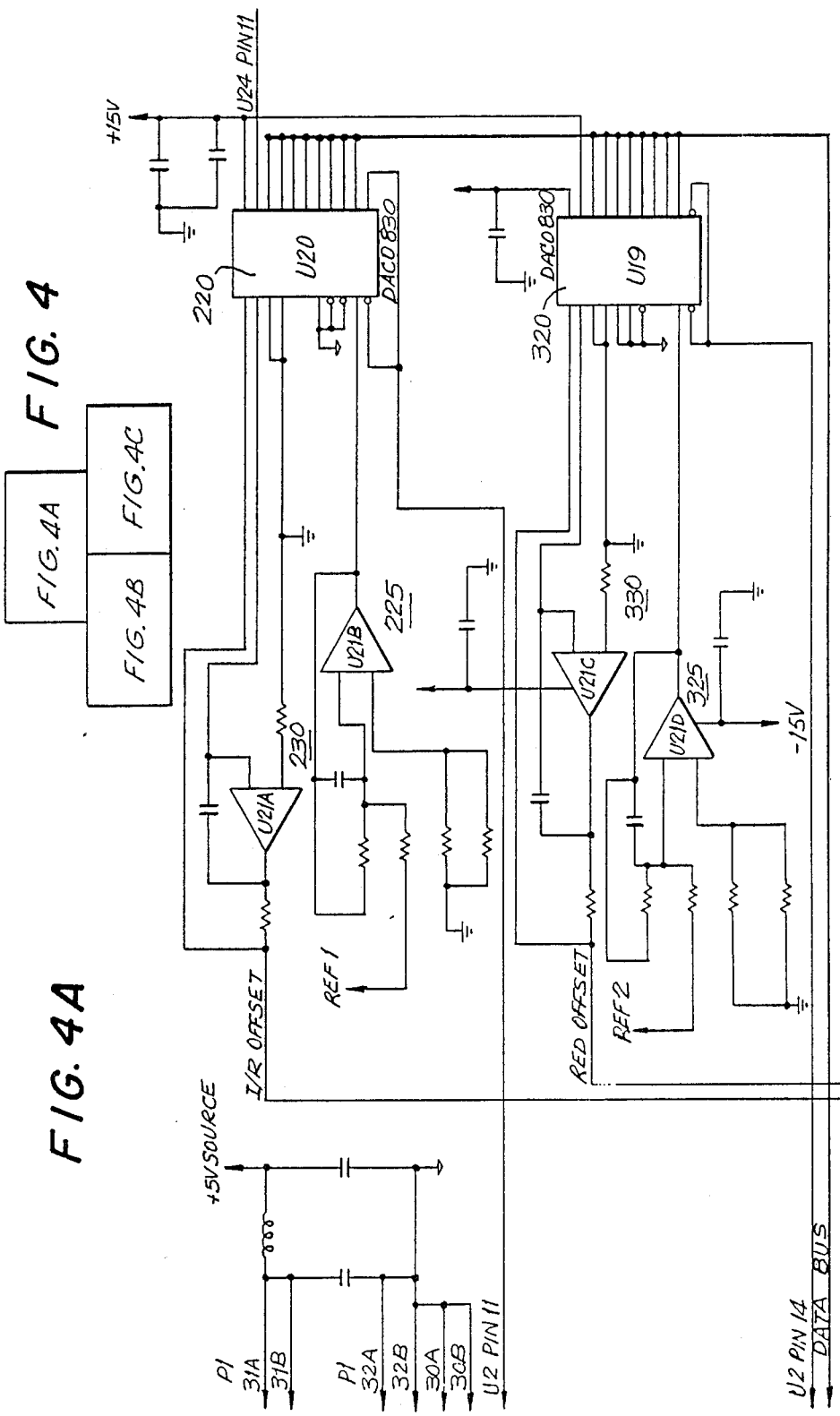

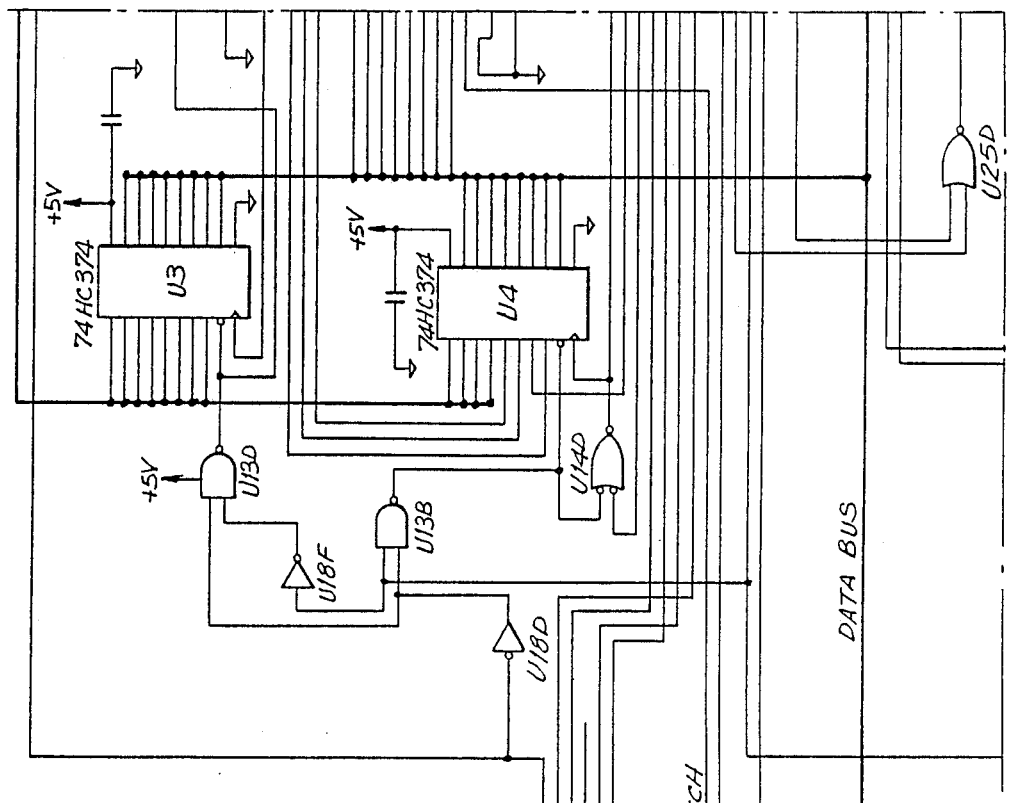
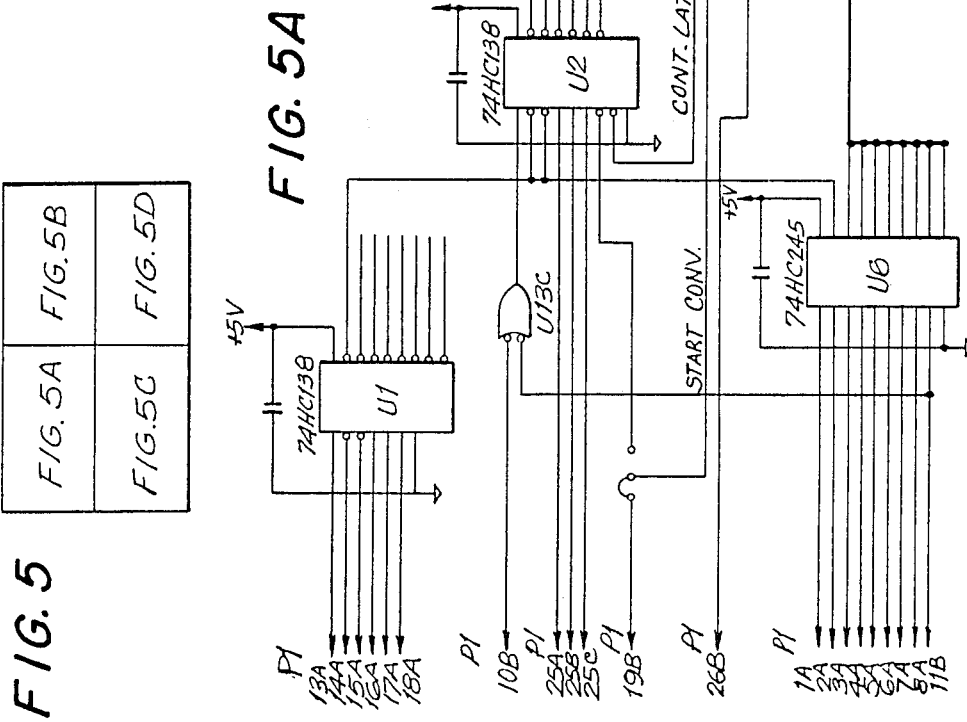
FIG. 5A
| FIG. 5A | FIG. 5B |
| --- | --- |
| FIG. 5C | FIG. 5D |
FIG. 5

APPARATUS AND METHOD FOR MEASURING BLOOD CONSTITUENTS

FIELD OF THE INVENTION

This invention relates to apparatus and methods for measuring the constituents of blood and, more particularly, apparatus for noninvasive determination of constituent concentrations utilizing light wave absorption measurements and methods for processing signals generated by such measurements.

BACKGROUND OF THE INVENTION

One known blood constituent measuring device is a blood oximeter which is a photoelectric photometer utilized for measurement of the fraction of hemoglobin in blood which is in the form of oxygenated Hb, that fraction is normally expressed in a percentage referred to as saturated oxygen content. The basic principles of blood oximetry based on these techniques are discussed in an article entitled ¢Oximetry" by Earl H. Wood, et. al., appearing at pages 416-455, Medical Physics, vol. 2, O. Glasser, Ed., Year Book Medical, Chicago, Ill (1960).

A number of oximetry devices and methods utilizing light in the red and infrared regions are shown in U.S. Pat. Nos. 3,638,640; 3,647,299; 3,704,706; 3,804,539; 3,998,550; 4,086,915 and 4,167,331.

Many previous oximetry devices use complex logarithmic functions to determine oxygen saturation of the blood as is shown, for example, in U.S. Pat. Nos. 3,638,140; 3,804,539; 3,998,550; and 4,167,331. The apparatus disclosed in U.S. Pat. No. 4,167,331 employs a digital microprocessor in conjunction with analog logarithmic amplifiers to calculate blood oxygen saturation. Other devices have utilized three frequencies, with synchronous detection, peak detection and ratio circuits, for example, that shown in U.S. Pat. No. 3,647,299.

Finally, there are blood oxygen saturation measurement devices employing digital techniques including computer microprocessors for calculating pulse rate, oxygen saturation and confidence factors for those values (see European Patent Application Publication No. 0104771) and one such device further includes normalization of the DC signal components from each light source and an AC modulated test signal for testing the device (see U.S. Pat. No. 4,407,290).

Nevertheless, even those devices employing digital techniques have not proven to be completely satisfactory in delivering reliable, blood constituent measurements particularly in the operating room environment. Therefore, a need exists for a compact, highly noise resistant, accurate and reliable blood constituent measurement apparatus and method.

SUMMARY OF THE INVENTION

This invention provides an apparatus and method for measuring variations in the opacity of blood due to blood volume changes related to Traube-Herring waves, respiration, heart pulsation, and hydrostatic pressure. Data relating to opacity variations is obtained by passing light of known wavelengths through blood containing tissue such as a finger or earlobe. For the purpose of determining the saturated oxygen content of the blood, the cyclic variations due only to the heart pulsations are extracted from the measurements and are corrected for the effects of the Traube-Herring waves. Calculation of heart rate and saturated oxygen content is performed using a programmed microprocessor. The same microprocessor also dynamically controls the data measurement function in a manner that optimizes the measurements under a variety of changing conditions.

It is therefore a principle object of the invention to provide a blood constituent measurement method and apparatus that is dynamically adaptive to the measurement environment.

It is a further object of the invention to continuously monitor and evaluate the quality of the measured values and display the result of such evaluation as a signal confidence level. It is also an object of the invention to utilize the signal quality evaluation to adjust the measurement parameters and signal analysis so as to obtain and maintain the highest signal confidence level.

It is a further object of the invention to measure and evaluate the presence of non-measurement signal noise and to adapt the measurement sequence so as to minimize interference of data acquisition by such noise.

It is still a further object of the invention to provide pulse rate data and blood oxygen saturation data along with a continuous indication of the confidence level in the accuracy of that data.

BRIEF DESCRIPTION OF THE DRAWINGS

These and other objects and advantages of the present invention are apparent from a consideration of the entire specification and the following drawings in which.

DESCRIPTION

Figure 1:
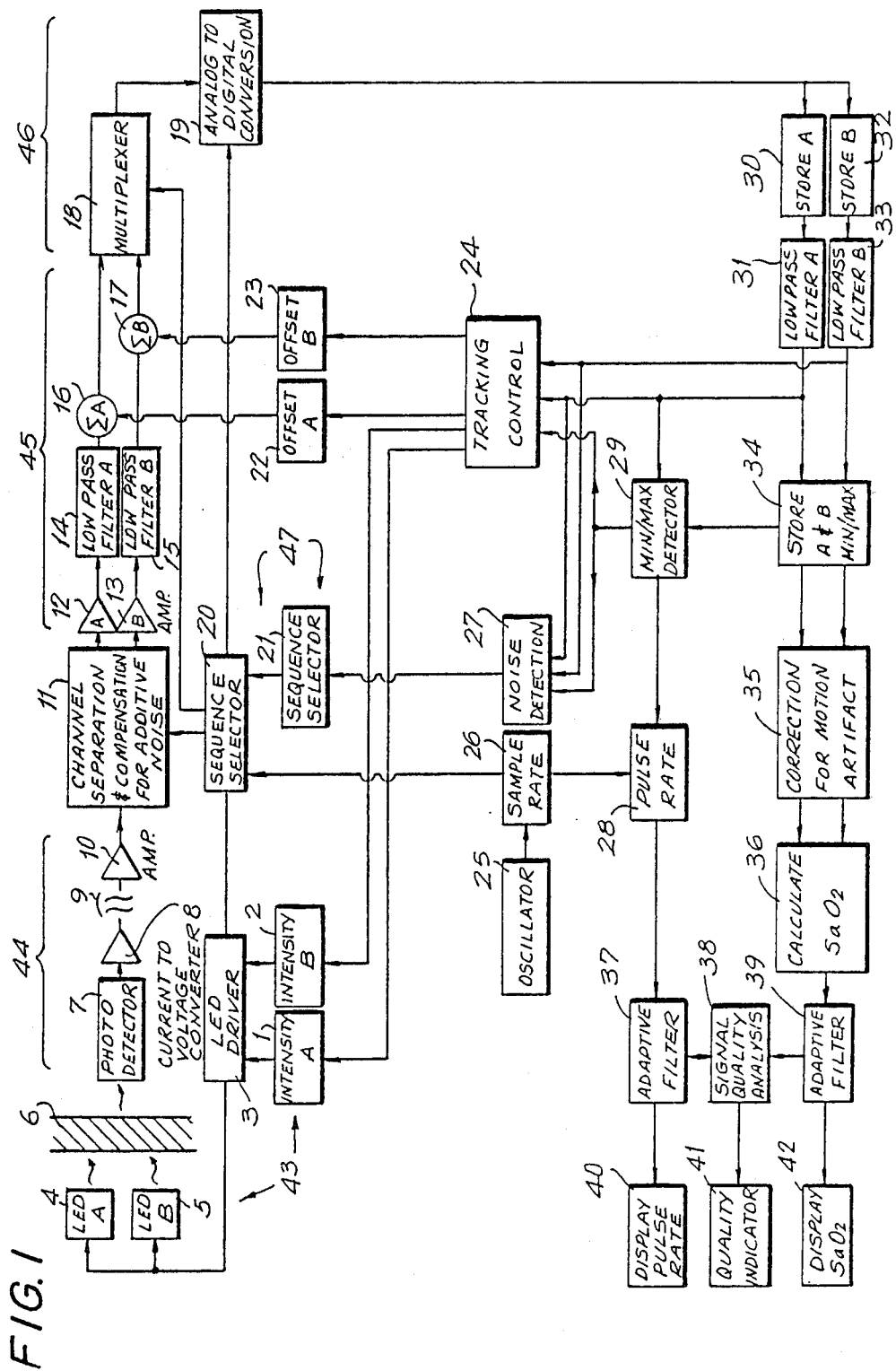
FIG. 1 is a Schematic Block Diagram of an apparatus of the invention.

Referring now to FIG. 1, there is shown in functional block diagram form an apparatus of the invention. The apparatus performs two functions simultaneously under the control of a programmed microprocessor (not shown); (1) control of signal generation; tracking the desired signal and measurement of the data provided by the signal (2) calculation of saturated blood oxygen level and pulse rate from the measured data and housekeeping functions associated with data display and operator interaction.

Broadly common to both of these functions is the circuitry to measure the raw data. This consists of the sequence control 47, LED control circuit 43, LED's 4, 5, a sample area causing pulsating changes in attenuation of the light 6, a signal detection method 44, channel separation and compensation for additive noise circuitry 11, analog signal processing circuits 45, and circuits to convert the signals to digital form 46.

The programmed microprocessor stores the data in memories 30 and 32, provides additional filtering to eliminate the noise associated with analog to digital conversion, 31 and 33, and detects inflection points to determine the minimum and maximum values of the plethysmographic waveform 29.

The microprocessor is also programmed to provide the tracking control 24 which is used to analyze the data to determine if the plethysmographic waveform is of sufficient amplitude and if the mean level of the signal at the input of the A/D convertor 19 is within an acceptable range. The tracking control program is also responsible for maintaining an acceptable amplitude for the pulse information by controlling the intensity of the LED's and adjusting the offset, 22 and 23, to maintain the signals within the acceptable range of the subsequent digital conversion circuits. These tasks are performed separately on each channel. The data necessary to make these decisions comes from the filtered digital signals from 31 and 33 as well as a separate determination of the amplitude of the plethysmographic waveform accomplished by the MIN/MAX detector 29. Tracking control and associated data acquisition is performed as a foreground task by the microprocessor.

The second function of the microprocessor is principally calculation and display of pulse rate 28, 37, 40 and calculation and display of saturated blood oxygen level ($SaO_2$) 36, 39, 42. A key part of the calculations process is determination and display of signal quality 38, 41. This function and the associated operator interaction are performed by the microprocessor as background tasks.

Figure 2B:
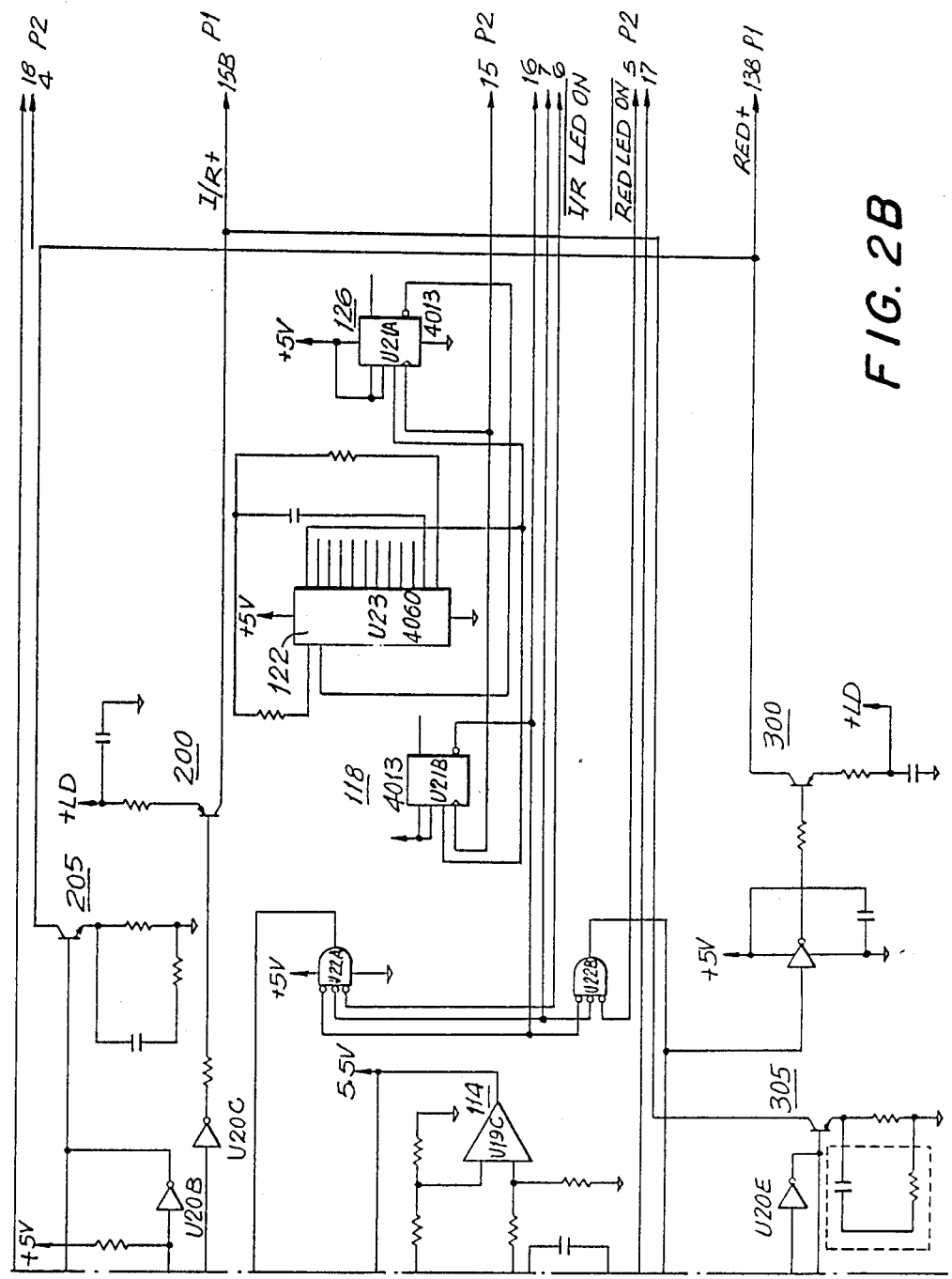
FIGS. 2A, B and C are a more detailed schematic diagram of components of the LED driver circuits shown in FIG. 1.
Figure 2C:
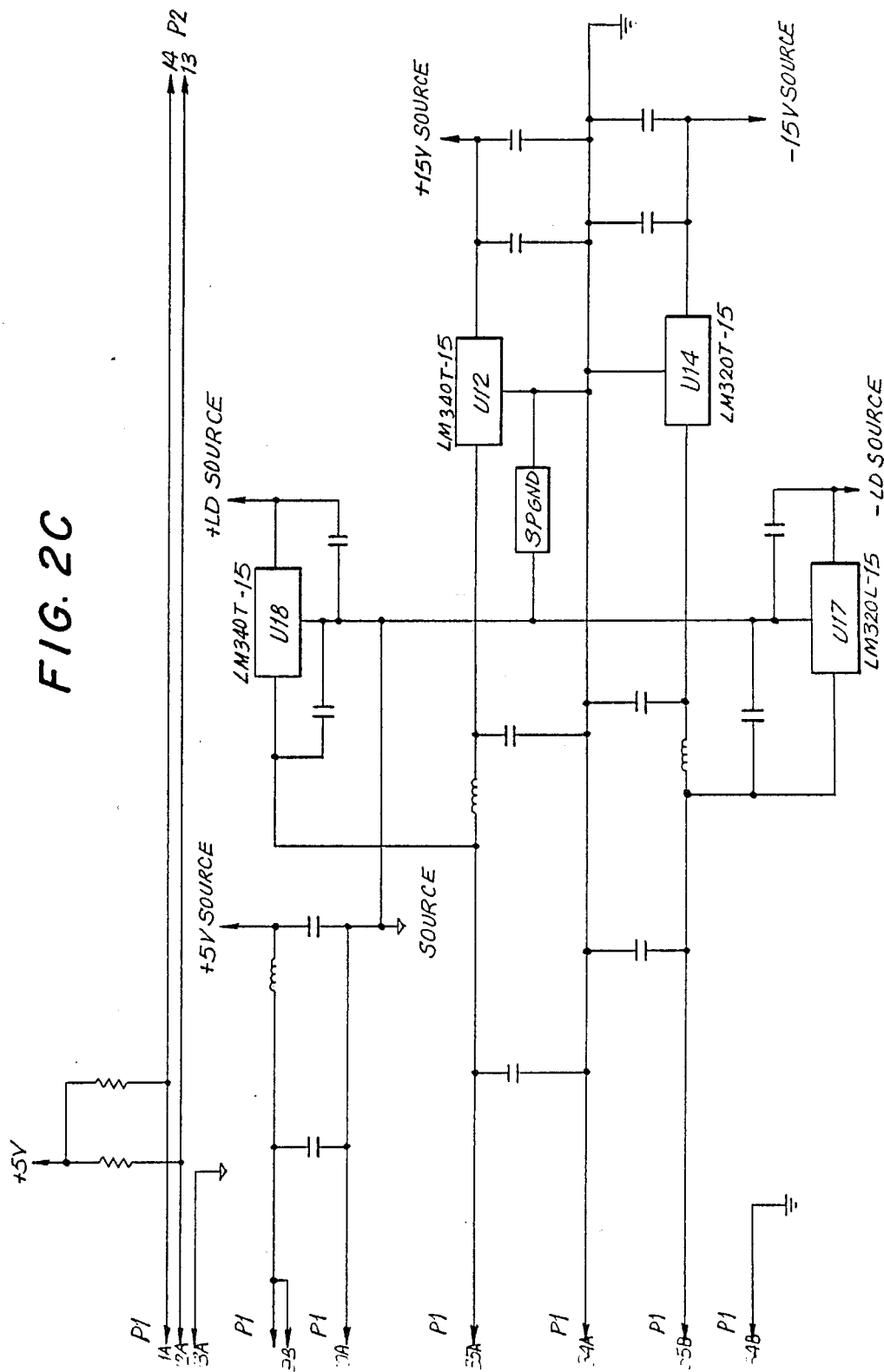
Figure 3B:
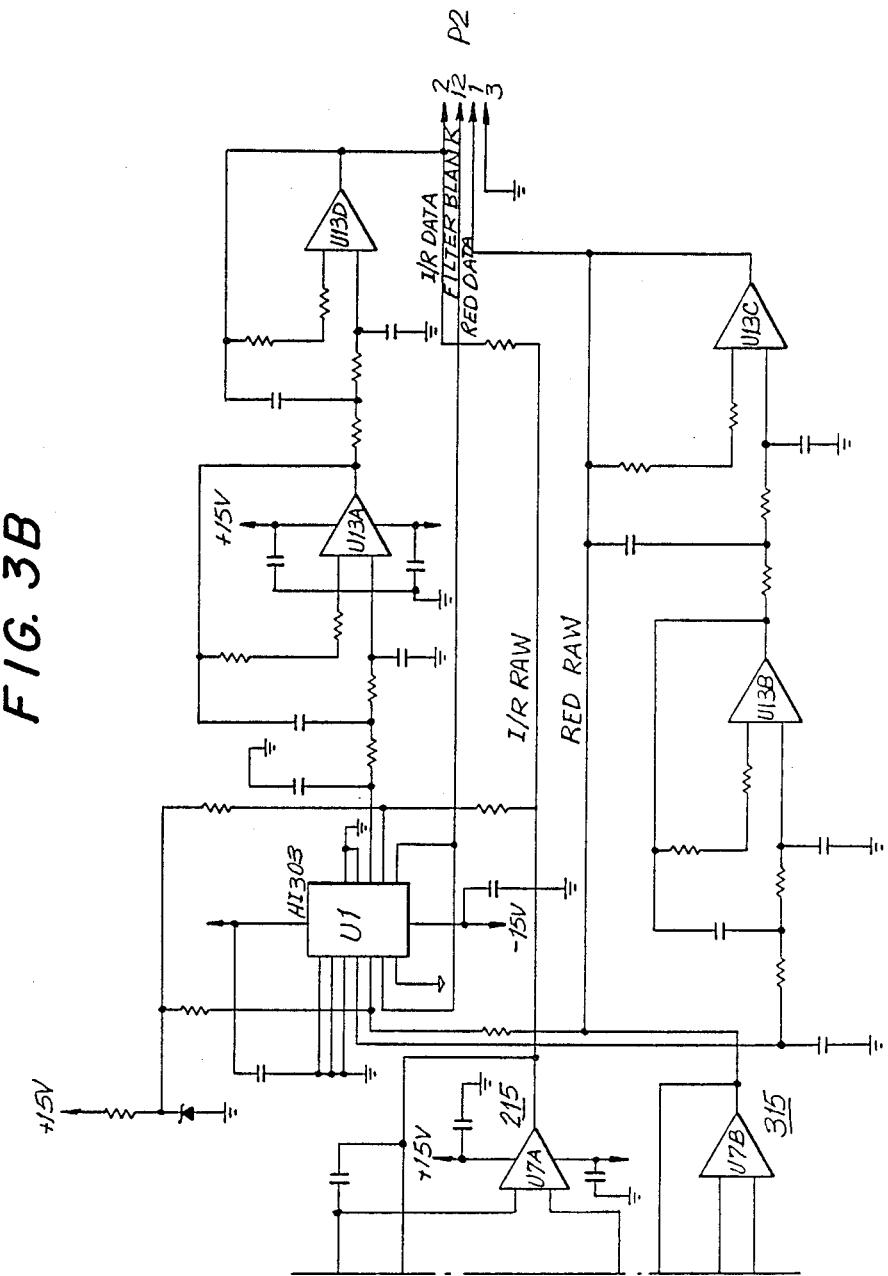
FIGS. 3A, B and C are a more detailed schematic diagram of components of the channel separation and compensation for additive noise circuits shown in FIG. 1.
Figure 3C:
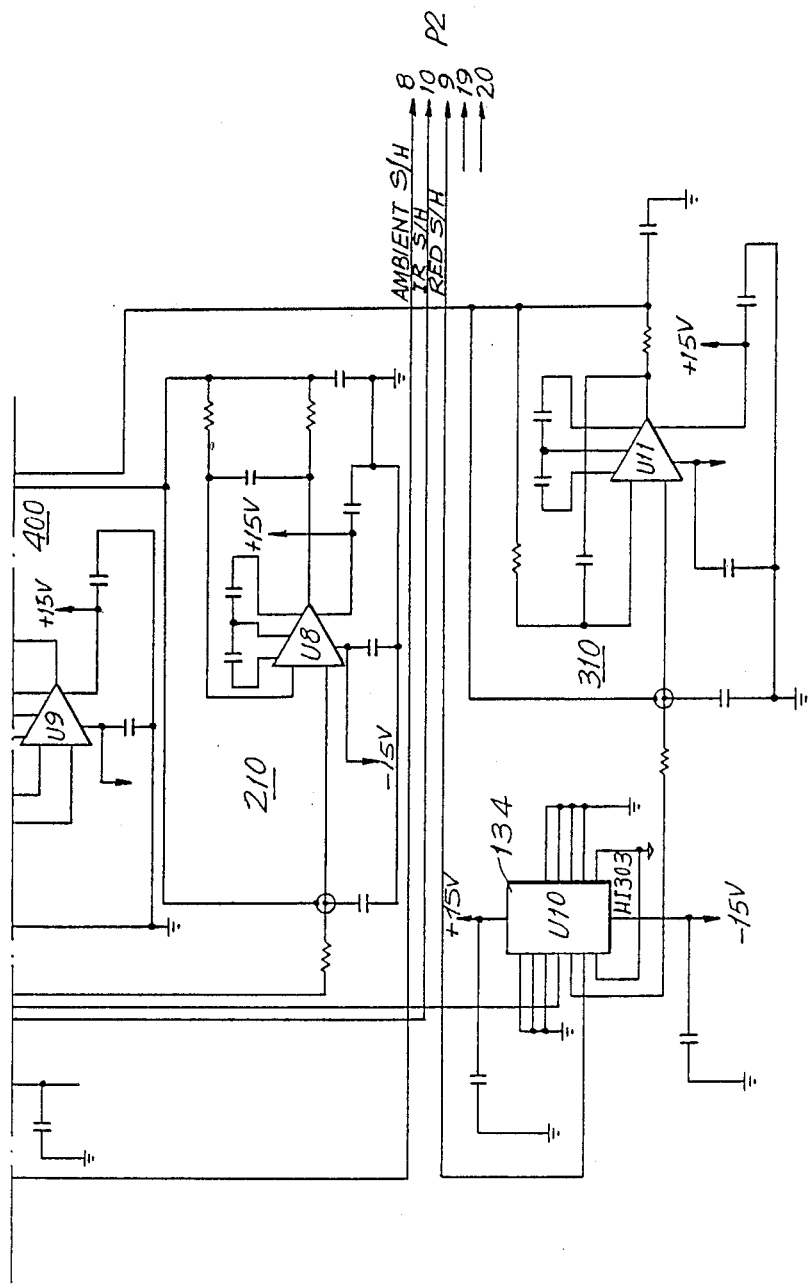

With the foregoing as an overview, the function of each block in FIG. 1 will be briefly described with reference to specific devices shown in FIGS. 2 and 3.

The light emitting diode (LED) control 43, controls the intensities of the individual light emitting diodes 4, 5, in response to signals generated by the Tracking Control 24. Each LED intensity is adjusted independently based on the data analyzed and received from that channel.

Referring to FIG. 1 there is shown intensity controls 1, 2 for LED's 4, 5 consisting mainly of a 12 bit digital to analog convertors, 100, 104, shown in FIG. 2A, which use a reference voltage 110 and 114 that has been temperature compensated to match the characteristics of the LED current drivers 3, particularly at low currents, and a circuit 50 for communicating with the microprocessor.

Returning to FIG. 1, the LED driver circuitry 3 assures predictable linear control over the maximum LED intensity range and minimizes the number of wires connecting the LED's to the instrument. A bipolar current driver, shown in FIG. 2B, for each data channel 200, 205, 300, 305 is used with associated components of a watchdog timer 118, 122 and 126 to insure that the LED's cannot remain on for extended time intervals at high currents, even in the event of a tracking or sequence control module failure. This is necessary to guarantee that the patient will not be burned and that the LED's will not be destroyed due to a momentary failure in the controlling software.

The light emitting diodes 4, 5, are composed of two RED (660 nm) dies wired in series and two INFRARED (940 nm) dies wired in series. The two diode pairs are mounted and wired in parallel but with opposite polarities on the same substrate and covered with an optically clear epoxy.

The received signals from the LED's as well as from any interfering sources are received by the photo detector 7, which is a standard PIN diode selected to be sensitive to light over the wavelengths from 600 nm to 1000 nm. The signal is amplified by a current to voltage convertor 8 and transmitted over a length of cable 9 to be received by an amplifier 10. The current to voltage convertor 8, is located in the cable assembly near the photo detector and is constructed as a hybrid to minimize the size and susceptibility to electromagnetic interference. The configuration is optimized to the frequency and gain requirements of the overall apparatus. The buffer amplifier 10, is used to amplify the signal by a factor of 20. The configuration of this amplifier is also optimized for frequency and noise requirements of the overall apparatus.

Channel separation 11 is performed on the amplified signal. The signals received by the amplifier 10 consist of a sequence of pulses determined by sequence selection and control circuitry, 47. The data collection sequence is ambient, ambient+RED, and ambient+INFRARED. This serially multiplexed data is separated by analog switches shown in FIGS. 3A and C, 130 and 134 and stored respectively in sample and hold elements 400, 210 and 310. These sample and hold circuits are unique in that the time constant for the circuit is many times greater than the sample period. In operation, the sampling circuit causes the signal to charge a capacitor through a resistive element for a predetermined short time period. The time constant of the R-C combination is many times longer than the sample period, therefor, many samples are required to charge the capacitor to a level representative of the original signal. The effect is to provide a high frequency filter near the sampled data frequency without distorting the desired data. Asymmetrical high frequency noise results in a constant residual value which will appear on all of the sampled and held signals and thus be cancelled in the subsequent subtraction operation. This unique method allows the three sets of data to be sampled nearly simultaneously while also filtering the data over a longer interval to remove any high frequency interference received by the photosensor. From the sample and hold elements the ambient data is subtracted from the INFRARED+ambient data by 215 and from the RED+ambient data by 315 both shown in FIG. 3B.

Returning to FIG. 1, after the data has been separated into two channels and compensated for additive noise at 11, it is further processed by elements designated analog signal processing circuits 45. Each channel is individually amplified by a factor of 5 by the difference amplifiers 12, 13. The RED channel data and INFRARED channel data are filtered by analog low pass filters 14, 15 to remove additional noise. These filters are of standard design and have been tuned for a cutoff frequency of approximately 10 Hz. This frequency was selected since the maximum heart rate expected to be measured will be 4 Hz.

Figure 4B:
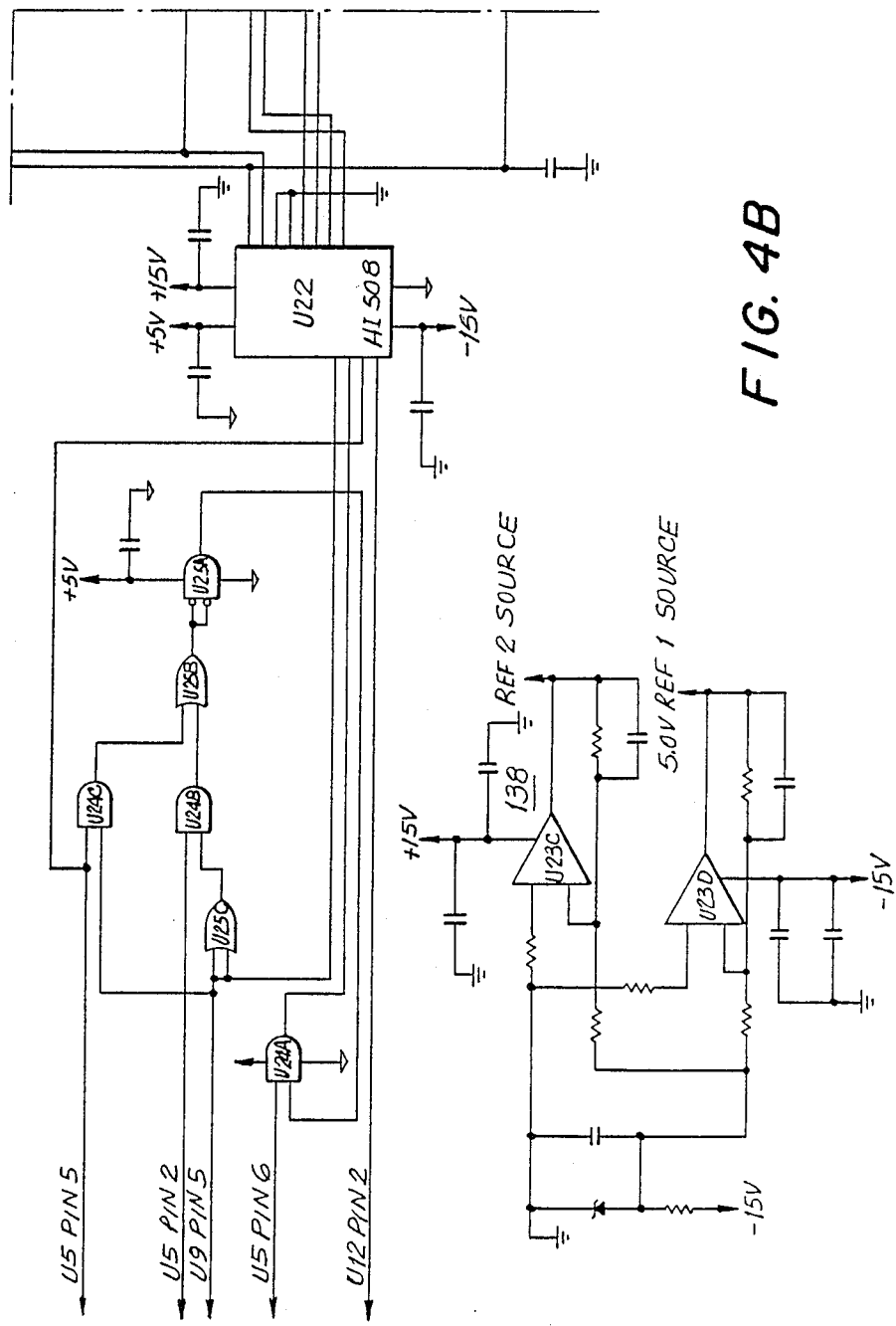
FIGS. 4A, B and C are a more detailed schematic diagram of the offset voltage circuitry shown in FIG. 1.
Figure 4C:
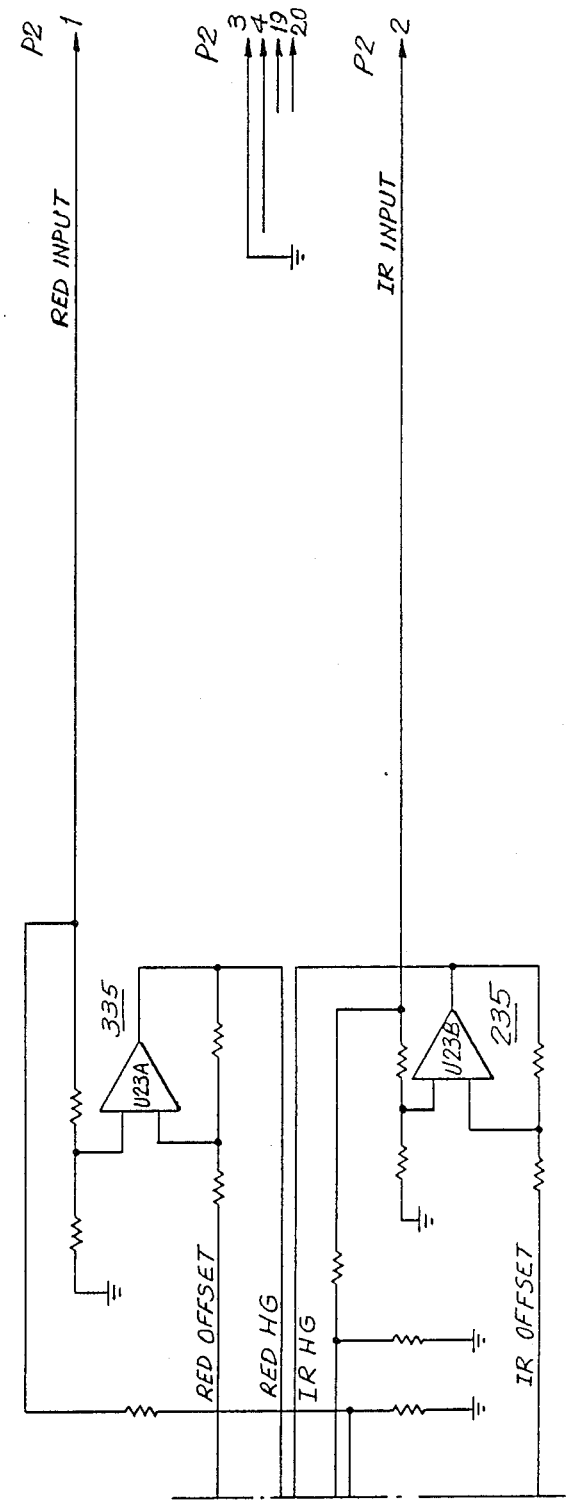

Offset voltages are generated for each channel in offset voltage sources 22, 23. Referring to FIG. 4 A, a precisely known voltage is generated by the digital to analog convertors 220 and 320 for each of the data channels. As shown in FIGS. 4A, B and C, the references for these voltages are developed by 138 and 225 and 325 for stability and to minimize crosstalk and noise between channels. The offset voltages are buffered by 230 and 330 and are made available to the difference amplifiers 235 and 335 as well as the multiplexer 18.

Returning to FIG. 1, the tracking control program in the microprocessor relatively corrects for the voltage present on each channel when no data is expected (both LED sources 4 and 5 and the offset voltages from 22 and 23 are turned off) by measuring it through common amplifiers 16, 17 and a common analog to digital convertor 19.

Up to this point, all of the signal processing has been accomplished by analog circuit techniques. Analog to digital conversion 46 is accomplished by directing the data to a common analog to digital convertor 19 by means of a multiplexer 18. Analog to digital conversion permits all subsequent data processing to be performed by the microprocessor.

The RED channel data and INFRARED channel data are directed by Multiplexer 18 to a common analog to digital convertor 19. In addition, the direct offset voltages are preset relative to Ref. 1 and Ref. 2 in the same A/D convertor, which permits calibration of the offset voltages relative to the same references used to measure the data.

Figure 5B:
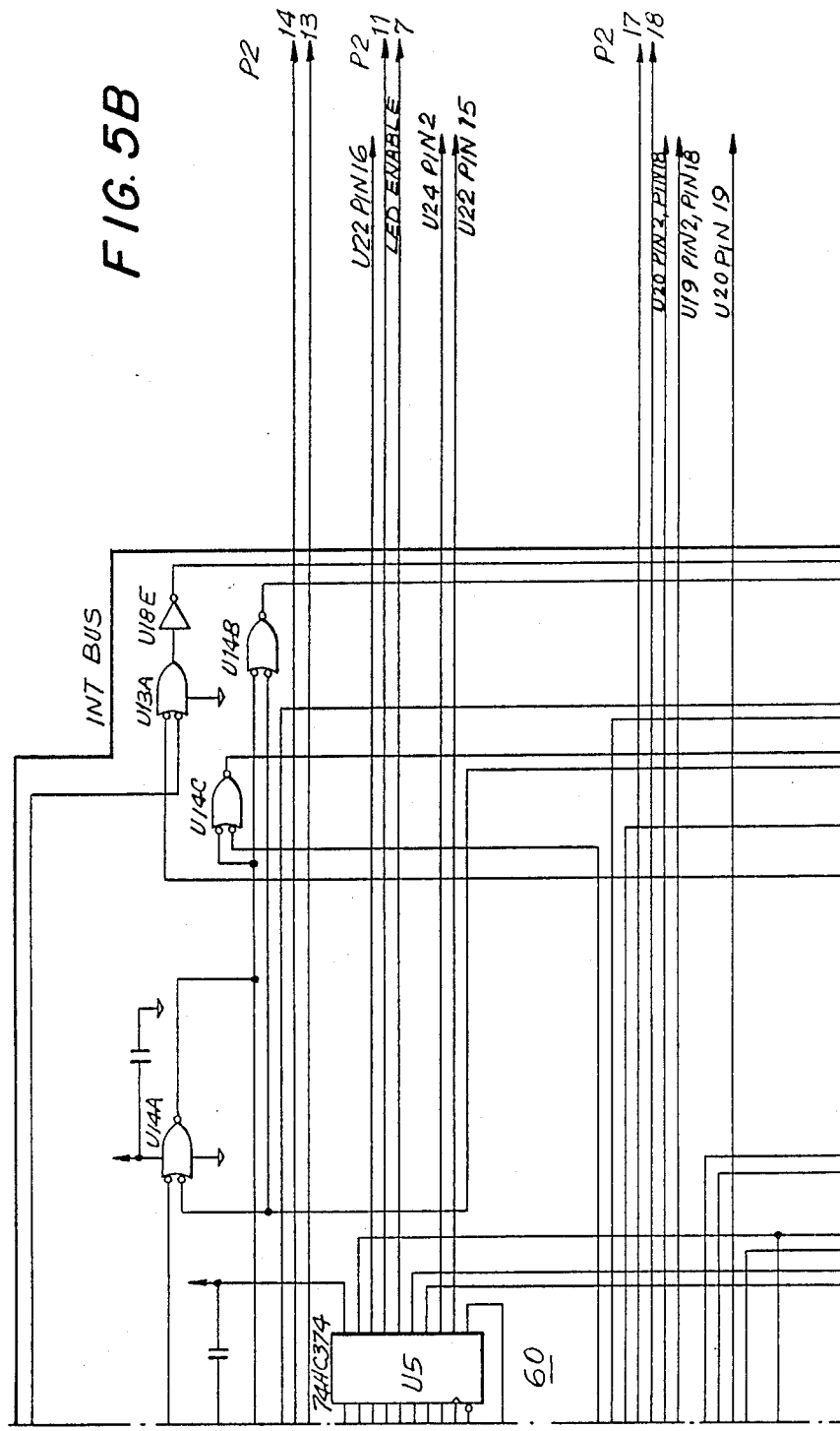
FIGS. 5A, B, C and D are a more detailed schematic diagram of the sequence control circuitry shown in FIG. 1.
Figure 5C:
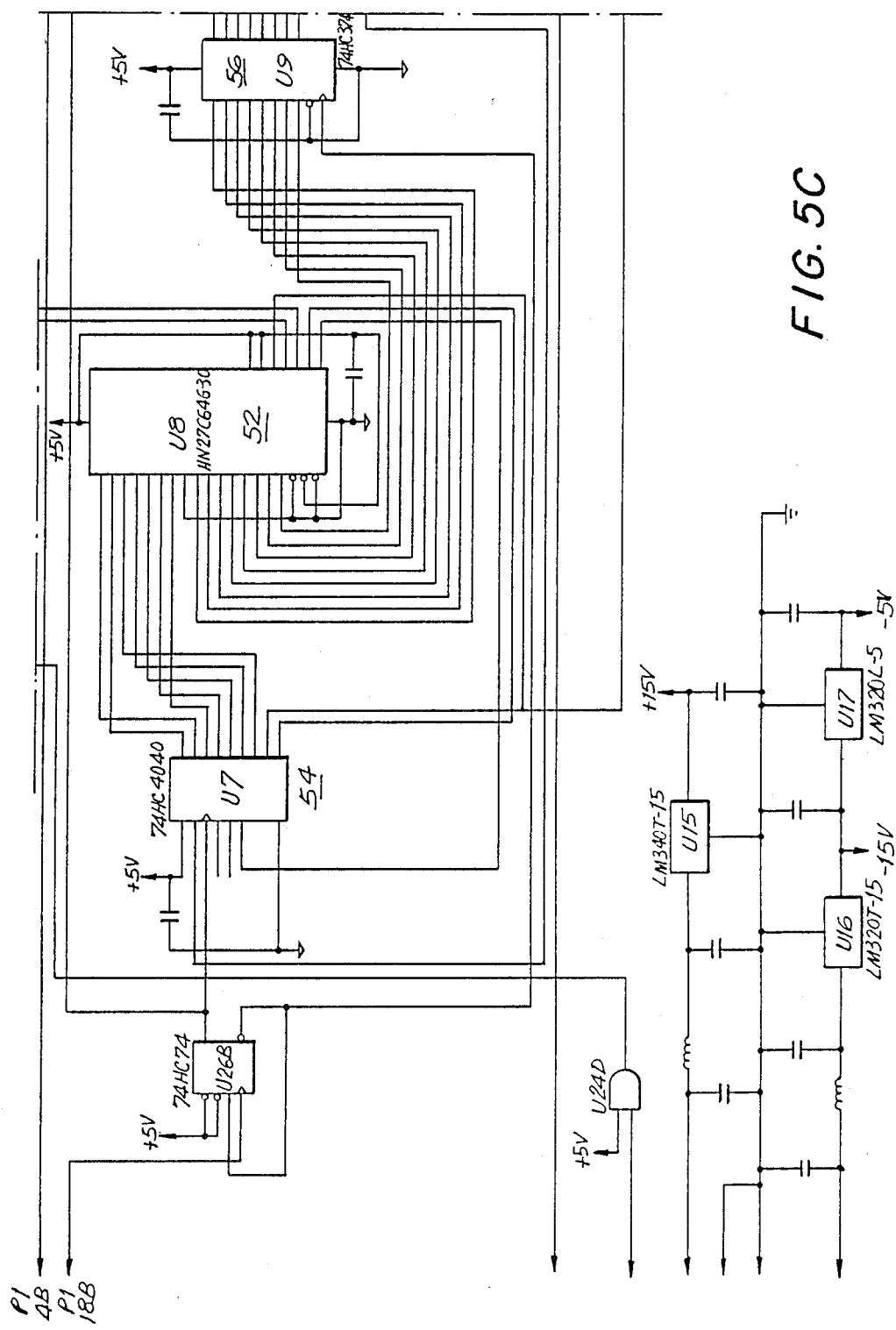
Figure 5D:
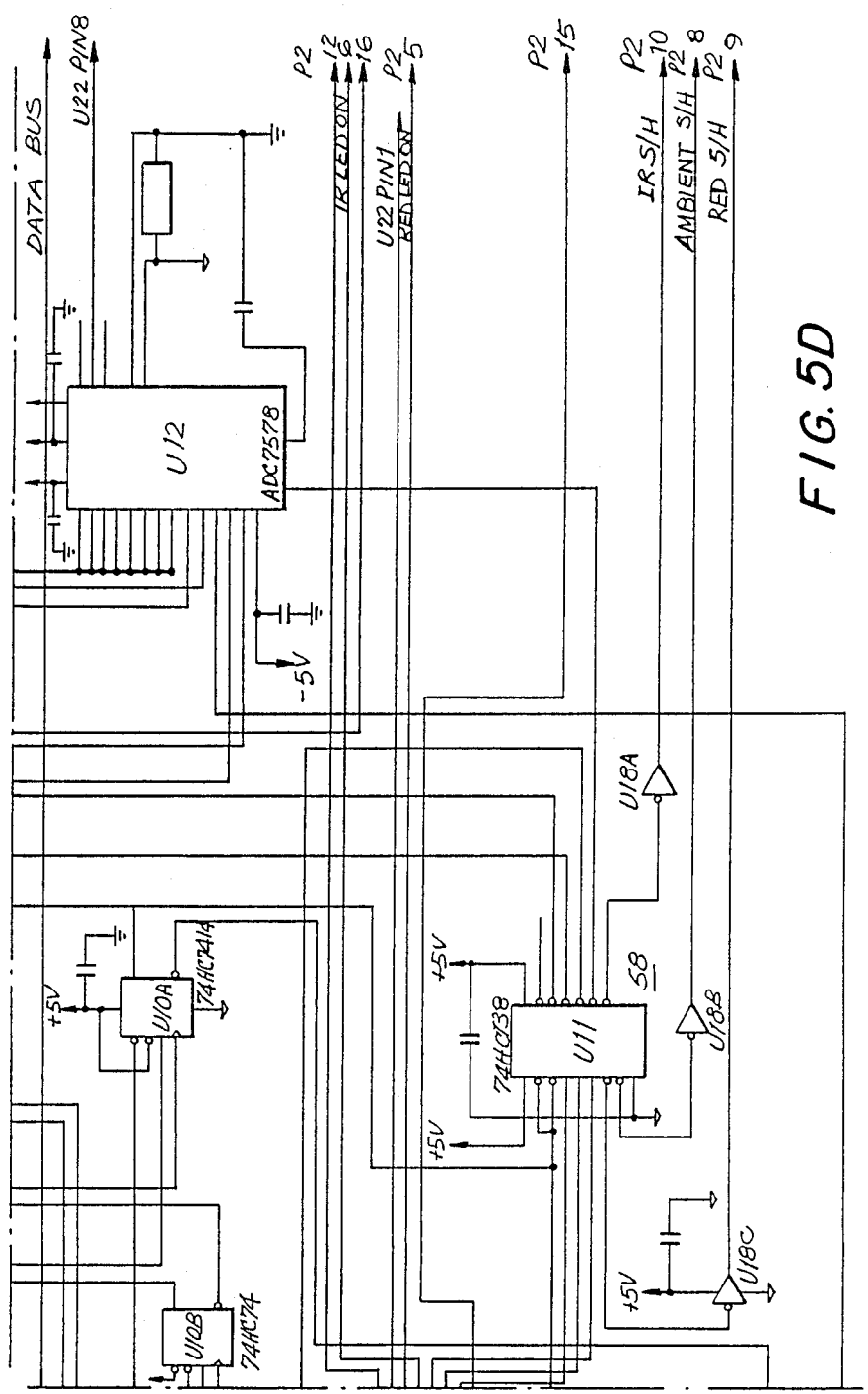

The operations of sequentially turning on the multiple diodes, 4, 5; receiving signals from the light emitted by the diodes and the ambient light; separating, sampling and holding this data 11; multiplexing the data 18; and converting the data by a common A/D convertor 19 for subsequent digital processing are all controlled by a sequence control circuit 20. Up to 4 unique sequences are provided to optimize the instrument for the particular measurement environment. Referring to FIG. 5C the sequence to be run is selected by sequence selection 21 from those stored in a Read Only Memory, 52. Upon initialization of the instrument, the counter 54 will increment through 1024 states for each sequence at a rate controlled by a clock synchronous with the microprocessor. At each counter increment the ROM 52 will yield a new pattern on 8 digital lines to be latched by 56. The outputs from latch 56 are used by sequence control 20 to control the operations of the LED drivers 3, sample and hold circuits 11, multiplexer 18, and A/D convertor 19. The end of the sequence is decoded by decoder 58 shown in FIG. 5D and an appropriate signal is sent to the microprocessor to indicate that the operation has been completed. Referring to FIGS. 5B and C, the selection of the desired control sequence is accomplished by selecting the appropriate starting address in the Read Only Memory 54 from the digital latch 60. The conditions for sequence selection and the purpose of the various sequences are discussed hereinbelow.

Returning to FIG. 1, the data from the A/D convertor 19 is separated and stored in memory buffers 30 and 32. This data is additionally filtered by digital lowpass filters 31, 32 to remove any noise created in the A/D conversion process.

At the onset of alarm conditions and at any time when the tracking control module determines that the instrument cannot track and obtain useful data from the subject, a test for the existence of outside interference is made by the Noise Detection module 27. As is explained more fully hereinbelow, this module selects a sequence in sequence selector 21 to cause the instrument to measure the amount of interference being received.

The MIN/MAX detector 29 samples the data points which are compared with data stored previously to determine if the data in question is a maximum value or a minimum value for that pulse cycle. When the MAX or MIN values are determined, they are stored for each channel in 34. The actual determination of MIN and MAX values is made on the INFRARED channel data only and the corresponding RED channel data points are stored. This operation assures that the subsequent calculations are made on related data even if they are not exactly at the maximum and minimum levels of the data received on the RED channel.

The oscillator 25 used to drive and synchronize the system is based on a crystal controlled clock that is an integral part of the computer.

The sample rate 26 of the data collection is based on the system oscillator and can be adjusted by the sequence control module of the microprocessor program.

The pulse rate module 28 analyses the information from the MIN/MAX detector 29 and scales it by the current sample rate to develop a continuously updated value representative of the subjects pulse rate.

Correction for motion artifact module 35 determines if an interference has occurred due to motion of the subject. This interference usually occurs as low frequency noise which is noise added to the data at a frequency lower than the desired data and is defined herein as less than 20 Hz. Errors caused by Traube-Herring waves are also in this frequency range and are also corrected for by this module.

Suppression of this type of noise is accomplished by comparing the current maximum value of the photoplethysmographic waveform for the infrared incident radiation with that of the proceeding waveform. If the relative level of the photoplethysmographic waveform maximum values are not with in a predetermined value, which is a predetermined percentage of the peak to peak amplitude of the first waveform, than the data calculated from the second waveform is not used.

The minimum and maximum values, including the offset value 22 and 23 subtracted from the data are used to calculate the value of the saturated oxygen in the subjects blood by the calculate $SaO_2$ module 36. The equation used is as follows:

$$RR = [\log(REDmax/REDmin)]/[\log(INFRAREDmax/INFRAREDmin)]$$

$$SaO_2 A + B(RR) + C(RR)^2$$

Where the constants "A", "B" & "C" are determined from experimental data and are dependent upon the actual wavelengths of the LED's. The values of these constants are stored in Read Only Memory and are accessed by the microprocessor in performing these calculations.

The value of the $SaO_2$ resulting from calculation module 36 is filtered by a lowpass adaptive filter 39 with a cutoff frequency selected to be slightly greater than the most rapid change expected in the saturated oxygen of a human subject. Similarly, the value of the pulse rate from 28 is filtered by pulse adaptive filter 37 with a cutoff frequency slightly higher than the most rapid change expected in the pulse rate of a human subject. In addition each new data point is compared with the filtered value to determine if the data is within reason. If a data point (Dn) is determined to be outside of predetermined allowable limits, relative to previous data, the filtered value is not modified by the new data, however, the new data (Dn) is not discarded but is stored with a "flag", to indicate the direction of change for future reference. The next data point (Dn+1) is compared to the filtered data and again a determination is made. If the data (Dn+1) is within acceptable limits then the previously rejected data (Dn) is thrown out and the process continues. However, if the second data (Dn+1) is also outside the allowable limits it is compared to the previously questionable data (Dn). If the data are similar, i.e., within the same predetermined limits of each other, then the second data is stored. The process continues for a third time and if at that time the data is in the same direction as the two previous data points (Dn and Dn+1) it is assumed that the last three data points are to be considered as good data and the filter is biased to adjust its final value to be equal to the average of the last three data points.

The final value for $SaO_2$ is made available on a digital display 42 located on the front panel of the instrument.

Based on data from adaptive filters 37, 39, determinations are made by signal quality analysis module 38 to form a judgment on the quality, or accuracy, of the displayed data. Both the pulse rate and the calculated $SaO_2$ are examined for consistency and how those values deviate from the predetermined norm causes a quality value to be assigned.

The results of the quality analysis module 38 are displayed by signal quality indicator 41 as either a "∓*", "x" or a "+" depending on the assigned worth of the displayed data This quality indicator is based on the evaluated consistency of the pulse rate and $SaO_2$ values. If the $SaO_2$ value changes by more than 3% from the average a predetermined number of times or the pulse changes by more than 50 sample units a predetermined number of times, the quality indicator will drop accordingly. In each case, the change causes a variable called the change count to receive 1 point. If the values stay within range, the change count loses 1 point. If the value is out of range but is in the same direction as the previous value, no change is made to the count. Normally, both the pulse and $SaO_2$ change counters start with 4 points. The two counters are subtracted from the value 9 to arrive at a confidence value. For example, on start up the confidence is $9-4-4=1$. The lowest confidence value possible is 0 (values less than 0 are set to 0), while the highest is 9. The confidence levels are indicated on the meter display by changing the appearance of a display "needle" . A "+" is used to indicate confidence levels of 0 to 3, an "x" to indicate levels of 4 to 7, and an "*" to show high confidence of 8 or 9. The displayed symbol is caused to move horizontally as a representation of the raw data from 31 and 33. In this manner the heart beat of the subject is displayed as a arrhythmic motion from side to side of an indicator that is representative of the quality of the displayed data.

Referring again to FIG. 1, it can be seen that all of the modules discussed above are directly or indirectly controlled by tracking control module 24. It is responsible for maintaining an acceptable amplitude for the pulse information by controlling the intensity of the LED's and adjusting the offset, 22 and 23, to maintain the signals within the acceptable range of the subsequent circuits. These tasks are continuously performed separately on each channel. The data necessary to make these decisions comes from the filtered signals 31 and 33 as well as a separate determination of the amplitude of the plethysmographic waveform accomplished by the MIN/MAX detector 29. Specifically, the tracking control monitors the signals of both light sources independently to optimize the signal at each incident wavelength. This tracking of the signals is composed of two primary tasks: (1) to maintain a photoplethysmographic amplitude within predetermined limits, and (2) to adjust for signal offsets 16, 17, 22, 23 due to the variations in the transparency of the tissue sample and to adjust the amount of signal offset required to maintain the signals within the range of A/D converter 19.

Most significantly, the control flexibility provided by the tracking control module 24 interacting with the noise detection module 27 provides the apparatus of the invention with its unique capability of obtaining reliable data in the presence of the normally interfering noise found in the environments where such instruments are typically operated.

Initially, the apparatus is operated with the LED's 4 and 5 turned off. The signal received is measured noise that is processed in the same manner as measured data therefore a determination can be made as to the effect such noise would have on the data. If the noise is of such a magnitude or if it exceeds preset limits the apparatus turns off the data display and audibly and visually indicates that data cannot be gathered due to interfering noise.

The foregoing noise detection process is also performed periodically during the normal data collection process to indicate the presence of excessive noise and assure that reliable data is being measured. In addition, whenever the tracking control module 24 detects an abrupt drop in the results of the quality indicator calculation or any rapid change in measured physiological parameters a noise detection sequence is initiated.

As can be readily seen from the foregoing discussion the control, and data analysis functions are performed by a programmed microprocessor such as the 8086 microprocessor manufactured by the Intel Corporation. A series of program modules written for use with a microprocessor, such as the Intel 8086, running under a real time operating system, such as the RMX operating system sold by the Intel Corporation, provide all of the microprocessor controlled functions described in respect of FIG. 1. In particular it is the unique control of data generation by using analysis of the acquired data that provides the instrument of the invention with its surprisingly superior performance in a wide variety of measurement environments.

Figure 6:
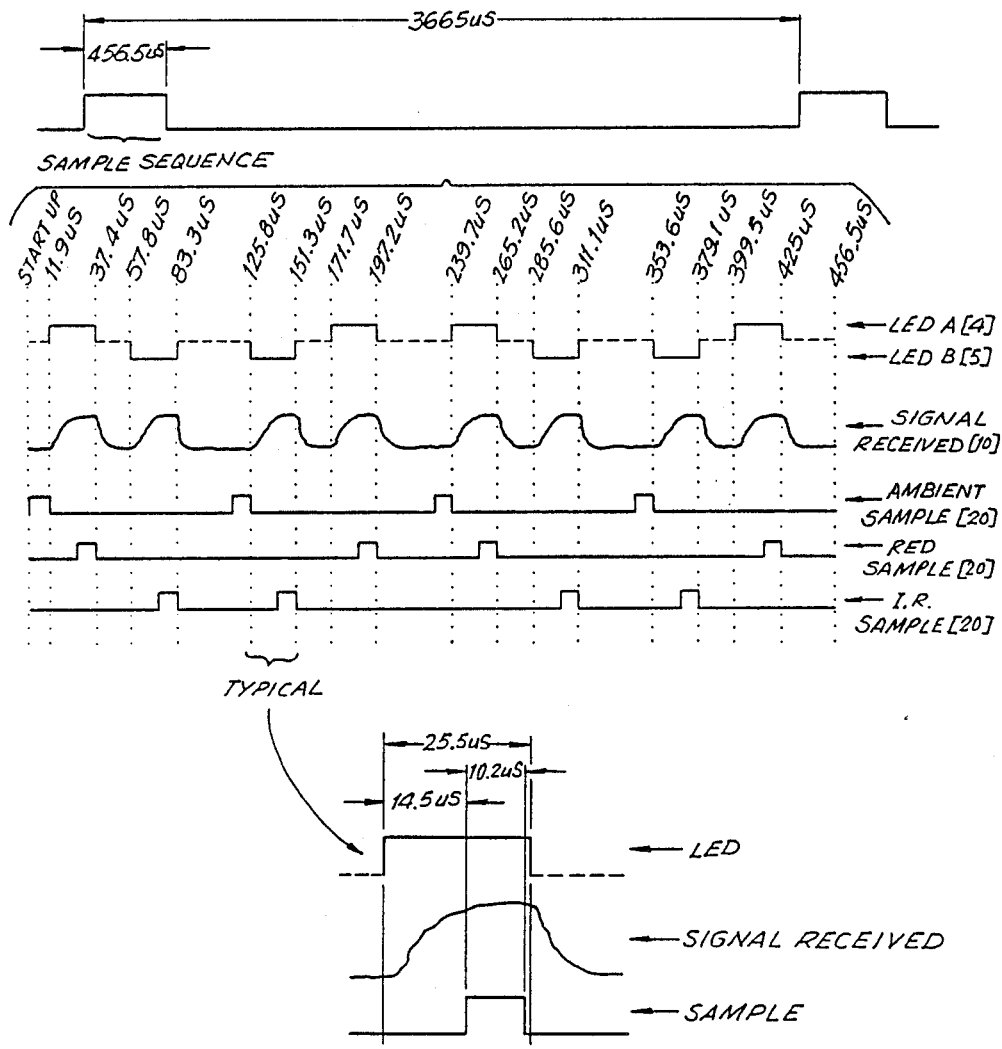
FIG. 6 is a timing diagram of a data collection sequence generated by the apparatus of FIG. 1.

Referring now to FIG. 6 there is shown an example of the Data Collection Sequence waveforms generated by the microprocessor. As can be seen a sample sequence time $t_s$ (456.5 $\mu$sec) occurs within an overall cycle time T (3665 $\mu$sec). During data collection the sequence controller causes multiple cycles of the "ambient-red-infrared" and ambient-infrared-red" sequence with the result that the time interval between measurement of ambient conditions and red or infrared light measurements are the same, on average, as stored in the averaging sample and hold circuits of FIG. 1 block 11.

Figure 7:
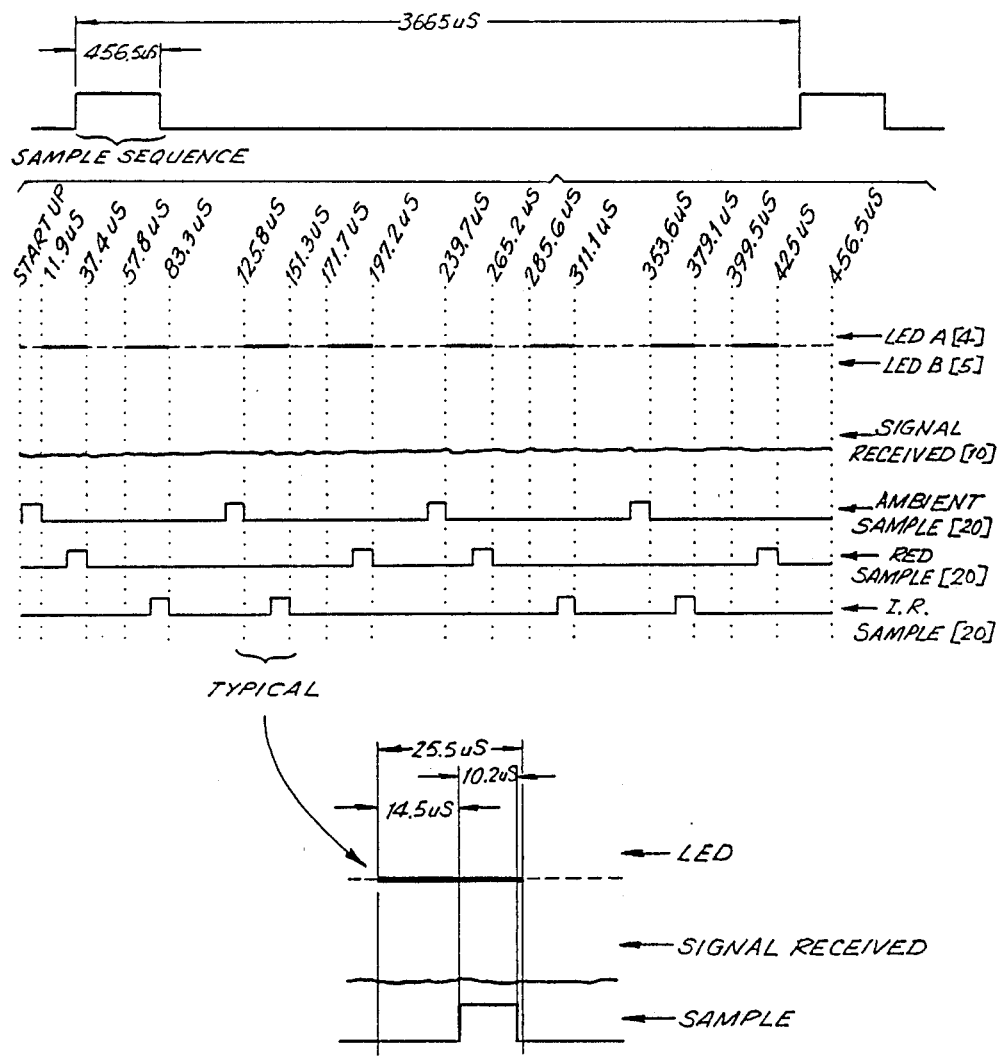
FIG. 7 is a timing diagram of the noise detection sequence caused by the noise detection and tracking control modules shown in FIG. 1.

Referring to FIG. 7 there is shown an example of the Noise Detection Sequence waveforms generated by the microprocessor. The sequence selected for measuring the amount of interfering noise is identical to that used in collecting the data, however, the LED's are never turned on. If there is no interfering noise the data available to the A/D converter will be close to zero in value.

We claim:

1. An apparatus for non invasive measurement of blood constituents in a living body comprising:
    (a) energy emitting means for emitting electromagnetic energy at a plurality of predetermined wavelengths;

(b) holder means for holding said energy emitting means and directing said electromagnetic energy through an area of living tissue containing flowing blood;
(c) detector means for receiving said electromagnetic energy through said area of living tissue and for producing electrical signals in response to receiving said predetermined wavelengths of electromagnetic energy;
(d) said detector means also receiving ambient electromagnetic energy and producing an electrical signal in response thereto;
(e) signal discriminating means connected to said detector means for separating said electrical signals;
(f) storage means connected to said signal discriminating means for storing said separated signals;
(g) subtraction means connected to said storage means for subtracting said ambient electrical signal from said predetermined wavelength electrical signals to produce data signals;
(h) signal processing means connected to said signal discriminating and signal storage means for amplifying, filtering and conditioning said data signals for further processing;
(i) electrical signal conversion means connected to said signal processing means for converting said data signals to digital data signals;
(j) first control means connected to said energy emitting means and said signal processing means for controlling said energy emissions;
(k) second control means connected to said signal discriminating means and said storage means for controlling said signal separation and storage, to said signal processing means for controlling said signal processing and to said signal conversion means for controlling said signal conversion;
(l) programmable digital arithmetic computation processor means connected to said signal conversion means for receiving said digital data signals and connected to said first and second control means for programmed direction of said control means;
(m) memory means connected to said digital arithmetic processor means for storing program processes;
(n) program processes stored in said memory means for analyzing said digital data signals, for detecting the presence of noise in said signals and for directing said first and second control means whereby said predetermined wavelength electrical signals are produced and received to the exclusion of said ambient electrical signals and said noise;
(o) program processes stored in said memory means for calculating from said predetermined wavelength data signals preselected blood constituent levels; and
(p) display means connected to said processor means for displaying the results of said preselected blood constituent level calculations.

2. The apparatus of claim 1 wherein the presence of noise is detected by deenergizing said energy means, processing the signals received, and directing said display means on the basis of the results to not display data and indicate the presence of excessive noise.

3. The apparatus of claim 1 wherein said processor means directs said control means to produce ambient and predetermined wavelength signals in a plurality of sequences whereby optimum data signals are obtained.

4. An apparatus for non invasive measurement of blood constituents in a living body comprising:
(a) energy emitting means for emitting electromagnetic energy at a plurality of predetermined wavelengths;
(b) holder means for holding said energy emitting means and directing said electromagnetic energy through an area of living tissue containing flowing blood;
(c) detector means for receiving said electromagnetic energy through said area of living tissue and for producing electrical signals in response to receiving said predetermined wavelengths of electromagnetic energy;
(d) said detector means also receiving ambient electromagnetic energy and producing an electrical signal in response thereto;
(e) signal discriminating means connected to said detector means for separating said electrical signals;
(f) signal sampling and storage means connected to said signal discriminating means for sampling and storing said separated signals;
(g) subtraction means connected to said storage means for subtracting said ambient electrical signal from said predetermined wavelength electrical signals to produce data signals;
(h) signal processing means connected to said signal discriminating and signal storage means for amplifying, filtering and conditioning said data signals for further processing;
(i) electrical signal conversion means connected to said signal processing means for converting said data signals to digital data signals;
(j) first control means connected to said energy emitting means and said signal processing means for controlling said energy emissions;
(k) second control means connected to said signal discriminating means and said storage means for controlling said signal separation and storage to said signal processing means for controlling said signal processing and to said signal conversion means for controlling said signal conversion;
(l) programmable digital arithmetic computation processor means connected to said signal conversion means for receiving said digital data signals and connected to said first and second control means for programmed direction of said control means;
(m) memory means connected to said digital arithmetic processor means for storing program processes;
(n) program processes stored in said memory means for analyzing said digital data signals, for detecting the presence of noise in said signals and for directing said first and second control means whereby said predetermined wavelength electrical signals are produced and received to the exclusion of said ambient electrical signals and said noise;
(o) program processes stored in said memory means for calculating from said predetermined wavelength data signals preselected blood constituent levels; and
(p) program processes stored in said memory means for selecting said predetermined wavelength data signals so as to suppress the Traube-Herring effect and calculating said preselected blood constituent levels from said selected signals;

(q) display means connected to said processor means for displaying the results of said preselected blood constituent level calculations.

5. The apparatus of claim 4 wherein said signal sampling storage means have time constants that are longer than the sample period whereby said means provide a high frequency noise filter at a frequency near the sampled data frequency without distorting the desired data.

6. The apparatus of claim 4 wherein said signals are selected by using data at the minimum photoplethysmographic wave point and then at the maximum wave point to calculate a first value of blood constituent level, using data at the next minimum wave point and the preceding maximum wave point to calculate a second value of blood constituent level, repeating said cycle of calculations to provide a final calculated blood constituent level which is averaged to suppress low frequency noise including the Traube-Herring effect.

7. An apparatus for non invasive measurement of blood constituents in a living body comprising:
 (a) energy emitting means for emitting electromagnetic energy at a plurality of predetermined wavelengths;
 (b) holder means for holding said energy emitting means and directing said electromagnetic energy through an area of living tissue containing flowing blood;
 (c) detector means for receiving said electromagnetic energy through said area of living tissue and for producing electrical signals in response to receiving said predetermined wavelengths of electromagnetic energy;
 (d) said detector means also receiving ambient electromagnetic energy and producing an electrical signal in response thereto;
 (e) signal discriminating means connected to said detector means for separating said electrical signals;
 (f) storage means connected to said signal discriminating means for storing said separated signals;
 (g) subtraction means connected to said storage means for subtracting said ambient electrical signal from said predetermined wavelength electrical signals to produce data signals;
 (h) electrical signal conversion means connected to said signal processing means for converting said data signals to digital data signals;
 (i) first control means connected to said energy emitting means and said signal processing means for controlling said energy emissions;
 (j) second control means connected to said signal discriminating means and said storage means for controlling said signal separation and storage to said signal processing means for controlling said signal processing and to said signal conversion means for controlling said signal conversion;
 (k) programmable digital arithmetic computation processor means connected to said signal conversion means for receiving said digital data signals and connected to said first and second control means for programmed direction of said control means;
 (l) memory means connected to said digital arithmetic computation processor means for storing program processes;
 (m) program processes stored in said memory means for analyzing said digital data signals, for detecting the presence of noise in said signals and for directing said first and second control means whereby said predetermined wavelength electrical signals are produced and received to the exclusion of said ambient electrical signals and said noise;
 (n) program processes stored in said memory means for calculating from said predetermined wavelength data signals preselected blood constituent levels;
 (o) adaptive filter means connected with said processor means level for evaluating the results of said preselected blood constituent level calculations with respect to the results of previous calculations and determining a value of the quality of the received signals based on such evaluation; and
 (p) display means connected to said processor means for displaying the results of said preselected blood constituent level calculations, and said signal quality value.

8. The apparatus of claim 7 including program processes for calculating from said predetermined wavelength data signals a pulse rate value, further including adaptive filter means connected with said processor means for evaluating the results of said pulse rate calculations with respect to the results of previous calculations, adjusting said value of the quality of the received signals on the basis of that evaluation, and wherein said display means displays the results of said pulse rate calculations and said adjusted signal quality value.

* * * * *

UNITED STATES PATENT AND TRADEMARK OFFICE
CERTIFICATE OF CORRECTION

PATENT NO. : 4,863,265

DATED : September 5, 1989

INVENTOR(S): Ronald J. Flower, Robert W. Olsen, Michael A. Van Ells
Ralph Flatau It is certified that error appears in the above-identified patent and that said Letters Patent is hereby corrected as shown below:

Column 1, line 21   "¢Oximetry" should read -- "Oximetry" --.

Column 2, line 43   "FIGS. 5A should be indented to indicate new paragraph.

Column 4, line 33   "therefor" should read -- therefore --.

Column 6, line 15   "analyses" should read -- analyzes --.

Column 6, line 18   "subjects" should read -- subjects' --.

Column 6, line 32   "with in" should read -- within --.

Column 6, line 34   "than" should read -- then --.

Column 6, line 37   "value" should read -- values --.

Column 6, line 45   "$SaO_2 A + B(RR) + C(RR)^2$" should read -- $SaO_2 = A + B(RR) + C(RR)^2$ --.

Column 7, line 25   "$\bar{+}*$" -should read -- "*" --.

UNITED STATES PATENT AND TRADEMARK OFFICE
CERTIFICATE OF CORRECTION

PATENT NO. : 4,863,265

DATED : September 5, 1989

INVENTOR(S): Ronald J. Flower, Robert W. Olsen, Michael A. Van Ells, Ralph Flatau It is certified that error appears in the above-identified patent and that said Letters Patent is hereby corrected as shown below:

```
Column 7, line 27    "data" should read -- data. --.

Column 8, line 17    "therefore" should read
                     -- , therefore, --

Column 8, line 31    "discussion" should read
                     -- discussion, --.

Column 8, line 32    "control, "should read -- control --.
```

UNITED STATES PATENT AND TRADEMARK OFFICE
CERTIFICATE OF CORRECTION

PATENT NO. : 4,863,265

DATED : September 5, 1989

INVENTOR(S) : Ronald J. Flower, Robert W. Olsen, Michael A. Van Ells
Ralph Flatau It is certified that error appears in the above-identified patent and that said Letters Patent is hereby corrected as shown below:

Column 8, line 35   "A series" should be indented to indicate a new paragraph.

Column 8, line 51   "ambient-infrared-red" should read -- "ambient-infrared-red" --.

Column 8, line 58   "microprocessor." should read -- microprocessor programmed in accordance with Appendix I.

Column 8, line 64   "non invasive" should read -- noninvasive --.

Column 10, line 1   "non invasive" should read -- noninvasive --.

UNITED STATES PATENT AND TRADEMARK OFFICE
CERTIFICATE OF CORRECTION

PATENT NO. : 4,863,265

DATED : September 5, 1989

INVENTOR(S) : Ronald J. Flower, Robert W. Olsen, Michael A. Van Ells, Ralph Flatau It is certified that error appears in the above-identified patent and that said Letters Patent is hereby corrected as shown below:

```
Column 10, line 63   "levels; and" should read
                     -- levels; --

Column 10, line 68   "signals;" should read --signals;
                     and --.

Column 12, line 31   "means level for" should read
                     --means for --
```

Signed and Sealed this

Tenth Day of December, 1991

Attest:

HARRY F. MANBECK, JR.

*Attesting Officer*      *Commissioner of Patents and Trademarks*